(12) United States Patent
Nakamura et al.

(10) Patent No.: US 7,179,326 B2
(45) Date of Patent: Feb. 20, 2007

(54) OXYGEN CONCENTRATION APPARATUS

(75) Inventors: Hitoshi Nakamura, Iwakuni (JP);
Masakazu Tagawa, Iwakuni (JP);
Katsuhiko Okada, Tokyo (JP)

(73) Assignee: Teijin Limited, Osaka (JP)

( * ) Notice: Subject to any disclaimer, the term of this patent is extended or adjusted under 35 U.S.C. 154(b) by 347 days.

(21) Appl. No.: 10/506,572

(22) PCT Filed: Mar. 5, 2003

(86) PCT No.: PCT/JP03/02583

§ 371 (c)(1),
(2), (4) Date: Sep. 3, 2004

(87) PCT Pub. No.: WO03/074113

PCT Pub. Date: Sep. 12, 2003

(65) Prior Publication Data

US 2005/0204923 A1    Sep. 22, 2005

(30) Foreign Application Priority Data

Mar. 5, 2002 (JP) ............................ 2002-058516
Jul. 31, 2002 (JP) ............................ 2002-222832

(51) Int. Cl.
*A61M 16/10* (2006.01)
*B01D 53/04* (2006.01)

(52) U.S. Cl. .................... 96/128; 96/380; 96/384; 124/204.15

(58) Field of Classification Search .................. 96/121, 96/126, 128, 380, 384; 95/96; 128/204.15, 128/204.18
See application file for complete search history.

(56) References Cited

U.S. PATENT DOCUMENTS 4,302,224 A    11/1981   McCombs et al.

(Continued)

FOREIGN PATENT DOCUMENTS

EP    0 185 980 A2    7/1986

(Continued)

OTHER PUBLICATIONS (Japanese) International Preliminary Examination Report for PCT/JP03/02583 completed on May 6, 2004.

(Continued)

*Primary Examiner*—Frank M. Lawrence
(74) *Attorney, Agent, or Firm*—Rader, Fishman & Grauer PLLC

(57) ABSTRACT

An oxygen concentrating apparatus 10 for generating oxygen enriched gas by adsorbing and separating nitrogen gas from air, comprises; an oxygen concentrator 40 having an adsorption cylinder filled with adsorbent for adsorbing nitrogen gas, also having an air inlet port 44, an oxygen outlet port 50 and a nitrogen gas outlet port 46; a compressor 30 for supplying compressed air from the air inlet port 44; a sound insulation box 20, which surrounds the compressor 30, for reducing noise generated from the compressor 30, ribs 20a being formed on a side wall of the sound insulation box 20; a cooling fan 36 for introducing air into the sound insulation box 20 so as to cool the compressor 30 by the introduced air; a housing 12 surrounding the oxygen concentrator 40 and the sound insulation box 20; and an exhaust duct 60 arranged in the housing 12, for guiding the exhaust discharged from the cooling fan 36 to the outside of the housing 12.

18 Claims, 3 Drawing Sheets

U.S. PATENT DOCUMENTS

| | | | |
|---|---|---|---|
| 4,342,573 A * | 8/1982 | McCombs et al. | 96/109 |
| 4,378,982 A * | 4/1983 | McCombs | 96/117 |
| 4,511,377 A * | 4/1985 | McCombs | 96/143 |
| 5,366,541 A * | 11/1994 | Hill et al. | 96/124 |
| 5,858,062 A * | 1/1999 | McCulloh et al. | 95/8 |
| 5,996,731 A * | 12/1999 | Czabala et al. | 181/229 |
| 6,311,719 B1 | 11/2001 | Hill et al. | |
| 6,478,857 B2 * | 11/2002 | Czabala | 96/130 |
| 2003/0200865 A1 * | 10/2003 | McCombs et al. | 95/121 |

FOREIGN PATENT DOCUMENTS

| | | | |
|---|---|---|---|
| EP | 185980 A2 | 7/1986 | |
| JP | 60-200804 A | 10/1985 | |
| JP | 63-49092 U | 4/1988 | |
| JP | 63-049092 U | 4/1988 | |
| JP | 02-211175 A | 8/1990 | |
| JP | 07-255851 A | 10/1995 | |
| JP | 2571757 Y2 | 2/1998 | |
| JP | 2571757 Y2 | 5/1998 | |
| JP | 11-285612 A | 10/1999 | |

OTHER PUBLICATIONS

International Search Report, mailed Jun. 17, 2003.

* cited by examiner

OXYGEN CONCENTRATION APPARATUS

TECHNICAL FIELD

The present invention relates to an oxygen concentrating apparatus used for medical treatment in which oxygen is concentrated from air by using adsorbent for selectively adsorbing nitrogen gas.

BACKGROUND ART

As one of the effective medical treatment methods to treat a patient for a disease of the respiratory such as pulmonary emphysema or chronic bronchitis, the medical treatment of oxygen inhalation is employed. In the medical treatment of oxygen inhalation, oxygen enriched gas, which is generated by separating nitrogen gas from air, is supplied to a patient. In order to accomplish this object, they have developed oxygen concentrators for generating oxygen enriched gas from air.

As an example of the oxygen concentrators described above, the U.S. Pat. No. 6,311,719 B1 describes a pressure swing adsorption (PSA) system provided with a plurality of nitrogen adsorption cylinders. For the medical treatment of oxygen inhalation conducted on a patient at home, a small oxygen concentrating apparatus, in which an oxygen concentrator and a compressor for supplying compressed air to the oxygen concentrator are combined with each other, has already been offered. Since this type oxygen concentrating apparatus is used at home, it is necessary to reduce the noise generated by the compressor and cooling fan.

In order to reduce the noise generated by each component of the oxygen concentrating apparatus, for example, the official gazettes of Japanese Unexamined Patent Publication Nos. 61-155204, 60-200804 and 2-211175 disclose an oxygen concentrating apparatus including: a sound insulation box made of metal surrounding a compressor and cooling fan; and an exhaust duct for guiding exhaust, which is sent from the cooling fan, to the outside, wherein the exhaust duct is formed into a bent passage having a plurality of bend sections.

However, the prior art described above has the following problems.

In the case where the sound insulation box made of metal surrounding the compressor and cooling fan is provided, when air is supplied from the compressor to the oxygen concentrator, pressure fluctuation is caused in the sound insulation box made of metal by the action of noise. Due to this pressure fluctuation, a side wall of the sound insulation box is vibrated especially in the low frequency region of 100 to 400 Hz. Therefore, the sound insulation box could become a new noise source.

When the plurality of bend sections are formed in the duct through which exhaust sent from the cooling fan is discharged, the exhaust noise generated from the cooling fan can be reduced, however, the entire size of the oxygen concentrating apparatus is extended, and the pressure loss of the duct is increased.

DISCLOSURE OF THE INVENTION

It is a technical task of the present invention to solve the above problems of the prior art. An object of the present invention is to provide an oxygen concentrating apparatus, the noise level of which is reduced while the oxygen concentrating apparatus is being downsized.

According to the present invention, there is provided an oxygen concentrating apparatus for generating oxygen enriched gas by adsorbing and separating nitrogen gas from air, comprising: an oxygen concentrator having an adsorption cylinder filled with adsorbent for adsorbing nitrogen gas, also having an air inlet port, an oxygen outlet port and a nitrogen gas outlet port; a compressor for supplying compressed air from the air inlet port; a sound insulation box, which surrounds the compressor, for reducing noise generated from the compressor, ribs being formed on a side wall of the sound insulation box; a cooling fan for introducing air into the sound insulation box so as to cool the compressor by the introduced air; a housing surrounding the oxygen concentrator and the sound insulation box; and an exhaust duct arranged in the housing, for guiding the exhaust discharged from the cooling fan to the outside of the housing.

According to another characteristic of the present invention, there is provided an oxygen concentrating apparatus for generating oxygen enriched gas by adsorbing and separating nitrogen gas from air, comprising: an oxygen concentrator having an adsorption cylinder filled with adsorbent for adsorbing nitrogen gas, also having an air inlet port, an oxygen outlet port and a nitrogen gas outlet port; a compressor for supplying compressed air from the air inlet port; a sound insulation box, which surrounds the compressor, for reducing noise generated from the compressor, ribs being formed on a side wall of the sound insulation box; a cooling fan for introducing air into the sound insulation box so as to cool the compressor by the introduced air; a housing surrounding the oxygen concentrator and the sound insulation box; and an exhaust duct arranged in the housing, for guiding the exhaust discharged from the cooling fan to the outside of the housing, wherein the exhaust duct includes a hollow outer shell having a horizontal portion and a perpendicular portion, which is connected to one end portion of the horizontal portion via one bend section so that the hollow outer shell can be extended into a substantial L-shape, and also includes a sound absorbing member of 2 to 20 mm thickness which is stuck onto an inner face of the hollow outer shell, the other end portion of the horizontal portion of the hollow outer shell is communicated with an outlet of air of the cooling fan, a lower end portion of the perpendicular portion is arranged in the housing so that it can be communicated with the exhaust port, and a cross sectional area of the exhaust duct is 12 to 20 cm² and the length of the exhaust duct is 350 to 450 nm.

MOST PREFERRED EMBODIMENT OF THE PRESENT INVENTION

Figure 1:
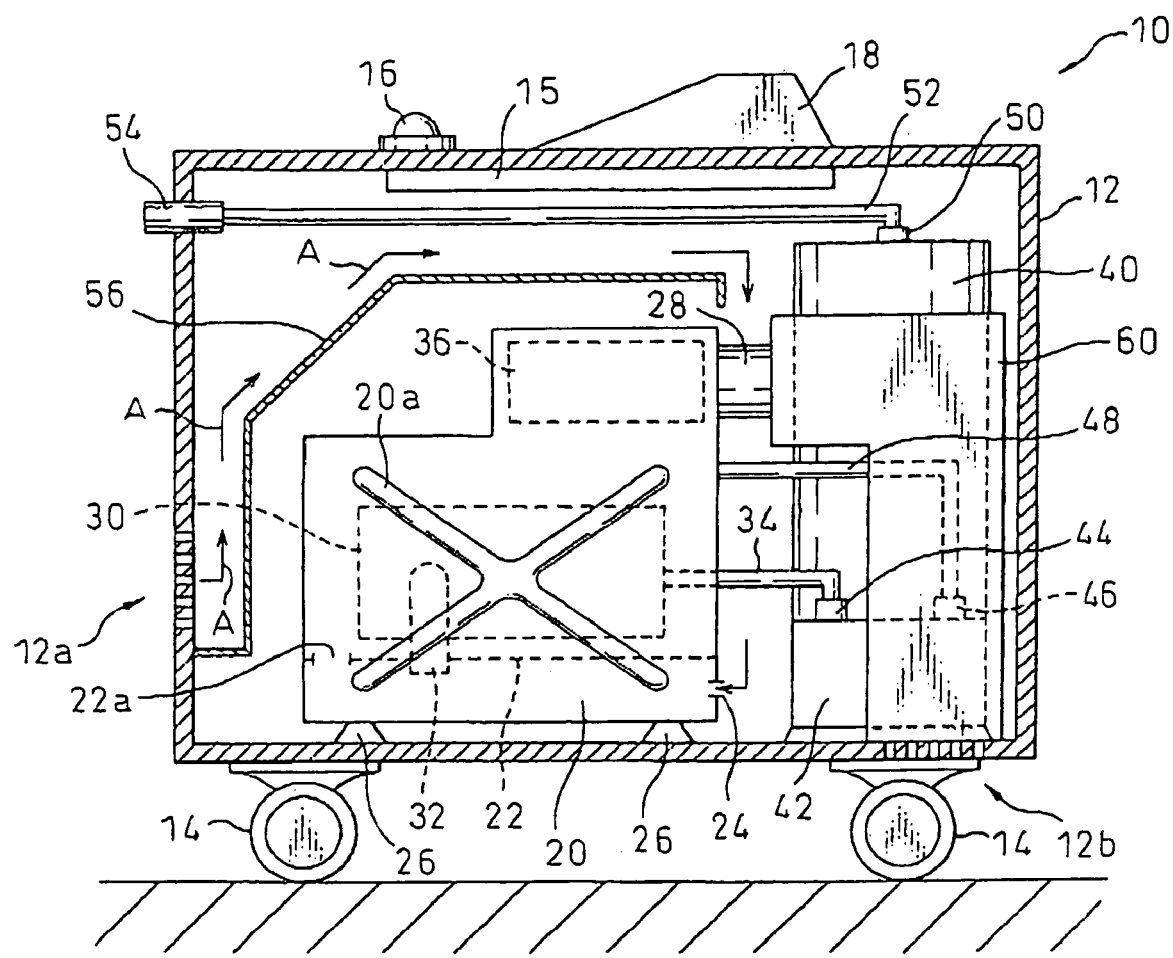
FIG. 1 is a view showing an outline of an oxygen concentrating apparatus of the present invention.

Referring to FIG. 1, the oxygen concentrating apparatus 10 of the most preferred embodiment of the present invention includes: a housing 12; an oxygen concentrator 40 arranged in the housing 12; a compressor 30 for supplying compressed air to the oxygen concentrator 40; a cooling fan 36 for circulating air in the housing 12 so as to cool the housing 12; an exhaust duct 60 for guiding exhaust sent from the cooling fan to the outside of the housing 12; and an electric control unit 15 for controlling the oxygen concentrator 40, the compressor 30 and the cooling fan 36.

The housing 12 includes: an air inlet 12a composed of a plurality of small halls formed on the side wall; and an exhaust port 12b composed of a plurality of small halls formed on the bottom wall. Onto the top wall of the housing 12, an ON-OFF switch for starting and stopping the oxygen concentrating apparatus 10 and one or a plurality of switches 16, which include the adjusting knob for setting a flow rate of condensed oxygen, are attached. Further, the display unit 18 is attached onto the top wall of the housing 12. The adjusting knob 16 and the display unit 18 are connected to the electric control unit 15. Further, a plurality of wheels 14 capable of freely moving the housing 12 are attached to the bottom wall of the housing 12.

It is possible to use various types of oxygen concentrators 40, however, it is preferable to use an oxygen concentrator having one or a plurality of adsorption cylinders filled with zeolite. In this connection, only one adsorption cylinder is shown in FIG. 1. For example, it is possible to use an oxygen concentrator, the brand name of which is AFT Module, which is available in the market from SeQual Technologies Inc., located in San Diego, Calif., wherein PSA system disclosed in U.S. Pat. No. 6,311,719 B1 is applied to this oxygen concentrator so that nitrogen gas can be separated from air. In this specification, the content of U.S. Pat. No. 6,311,719 B1 is incorporated by reference. Although the detail are not shown in FIG. 1, the oxygen concentrator 40 includes: one or a plurality of adsorption cylinders filled with adsorbent for selectively adsorbing nitrogen gas, for example, one or a plurality of adsorption cylinders filled with zeolite; an air inlet port 44; an oxygen outlet port 50; and a nitrogen gas outlet port 46. The oxygen outlet port 50 is fluidly communicated with an outlet port 54 of the oxygen concentrating apparatus 10 via an oxygen pipe 52.

Figure 2:
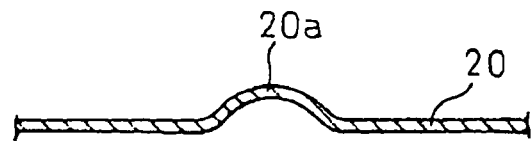
FIG. 2 is a sectional view showing a rib formed on a side wall of a sound insulation box.

The compressor 30 and the cooling fan 36 are surrounded by the sound insulation box 20 in the horsing 12. The sound insulation box 20 can be made of plastics or metallic material. The sound insulation box 20 includes; an air inlet opening 24 formed in a lower portion of one side wall; and an opening (not shown) forming an air outlet of the cooling fan 36 described later. At a position higher than the air inlet opening 24 in the sound insulation box 20, the partition wall 22 is horizontally arranged which partitions the inside of the sound insulation box 20 into an upper space and a lower space. In the partition wall 22, the cooling air passage 22a for fluidly communicating the upper space with the inner space is formed. As shown in FIGS. 1 and 2, on at least one side wall of the sound insulation box 20, ribs 20a are diagonally provided. Further, in the sound insulation box 20, the upper space on the upper side of the partition wall 22 is communicated with the nitrogen gas outlet port 46 of the oxygen concentrator 40 via the nitrogen gas pipe 48.

The compressor 30 is arranged on an upper face of the partition wall 22. The compressor 30 may be one of the reciprocating piston compressor, the rotary compressor, the scroll compressor, the screw compressor and the oscillating compressor. The compressor 30 includes: a suction pipe 32 penetrating the partition wall 22; and a discharge port (not shown) for discharging the compressed air, so that the upper space of the sound insulation box 20 can be communicated with the lower space which is lower than the partition wall 22 of the sound insulation box 20. The discharge port is connected to the air inlet port 44 of the oxygen concentrator 40 via the air supply pipe 34. It is preferable that the vibration proofing members 26 made of rubber or plastics are arranged between the compressor 30 and the upper face of the partition wall 22.

In the sound insulation box 20, the cooling fan 36 is arranged in an upper portion of the compressor 30. This cooling fan 36 can be an axial fan, a sirocco fan and so forth. The cooling fan 36 includes: an air inlet (not shown) arranged so that air can be sucked from the neighborhood of the compressor 30 in the upper space in the housing 12; and an air outlet (not shown) arranged so that the sucked air can be discharged to the outside of the sound insulation box 20. The air outlet is communicated with the exhaust duct 60 via a connecting pipe 28 made of rubber.

Figure 4:
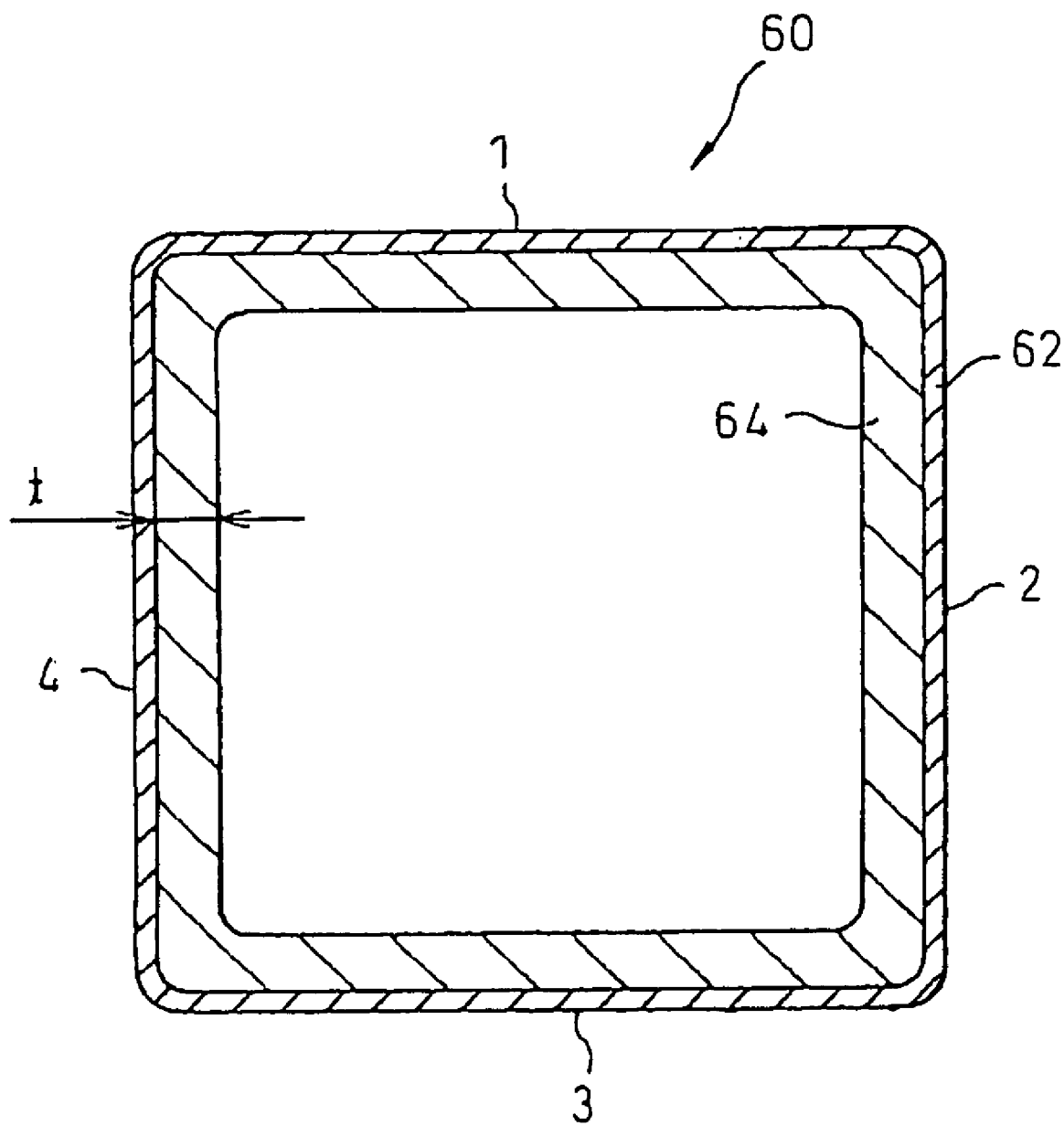
FIG. 4 is a sectional view of an exhaust duct.

The exhaust duct 60 is provided with an outer shell 62 (shown in FIG. 4) composed of a substantially L-shaped hollow member including a horizontal portion and a perpendicular portion which is connected to one end portion of the horizontal portion via one bend section. The connecting pipe is connected to an upper inlet of the hollow member. A lower exit of the hollow member is communicated with the exhaust port 12b. Referring to FIG. 4, the exhaust duct 60 includes: an outer shell 62, the cross section of which is a rectangle having side walls 1 to 4; and a sound absorbing member stuck onto the inner face of the outer shell 62. The outer shell 62 can be made of plastic materials such as acrylic nitrile butadiene styrene (ABS), polypropylene (PP), polyethylene (PE), polystyrene (PS), polybutylene terephthalate (PBT), and polyethylene terephthalate (PET). The outer shell 62 can be also made of metallic materials such as a plated steel sheet and an aluminum sheet. Alternatively, the outer shell 62 can be also made of wood. Alternatively, the outer shell 62 may be made of a compound material in which the above plastic materials and reinforced fiber such as glass fiber or carbon fiber are compounded with each other. Concerning the sound absorbing material, it is preferable to use porous plastic material. Especially, it is preferable to use soft urethane foam. In this connection, the exhaust duct illustrated in FIG. 4 has a rectangular cross section, however, the exhaust duct may have a circular cross section.

Operation of the present embodiment will be explained as follows.

When a user turns on ON-OFF switch of the oxygen concentrating apparatus 10, the compressor 30 and the cooling fan 36 are set in motion. Due to the start of the compressor 30 and the cooling fan 36, air in the periphery of the oxygen concentrating apparatus 10 is sucked from the air inlet 12a into the housing 12. It is preferable that the deflecting plate 56 is arranged in the housing 12 as shown in FIG. 1 and the air, which has flowed from the air inlet 12a into the housing 12, is moved upward toward the electric control unit 15 inside the housing 12 as shown by arrow A so that the electric control unit 15 can be cooled by the air.

Air that has flowed into the housing 12 is sucked from the air inlet opening 24, which is formed in a lower portion of the side wall of the sound insulation box 20, into the lower space in the sound insulation box 20. A portion of the air in the lower space on the lower side of the partition wall 22 in the housing 12 is sucked into the compressor 30 via the suction pipe 32 and compressed by the compressor 30. The air compressed by the compressor 30 is supplied to the oxygen condensation device 40 via the air supply pipe 34 and the air inlet port 44.

In the oxygen condensation apparatus 40, nitrogen gas is adsorbed and separated from air by the adsorbent, and oxygen enriched gas, the oxygen concentration of which is at least 90% (volume), is generated. This oxygen enriched gas is supplied to the output port 54 of the oxygen concentrating apparatus 10 via the oxygen outlet port 50 and the oxygen pipe 52. A user connects one end of a conduit tube (not shown) to the output port 54 and receives the oxygen condensation gas via a nasal mask (not shown) or nasal prong (not shown) connected to the other end of the conduit tube. The nitrogen gas adsorbed by the adsorbent is released from the adsorbent when the adsorbing cylinder is depressurized in the process of regenerating the adsorbent, and discharged into the upper space on the upper side of the partition wall 22 via the nitrogen gas outlet port 46 and the nitrogen gas pipe 48 in the sound insulation box 20.

Figure 3:
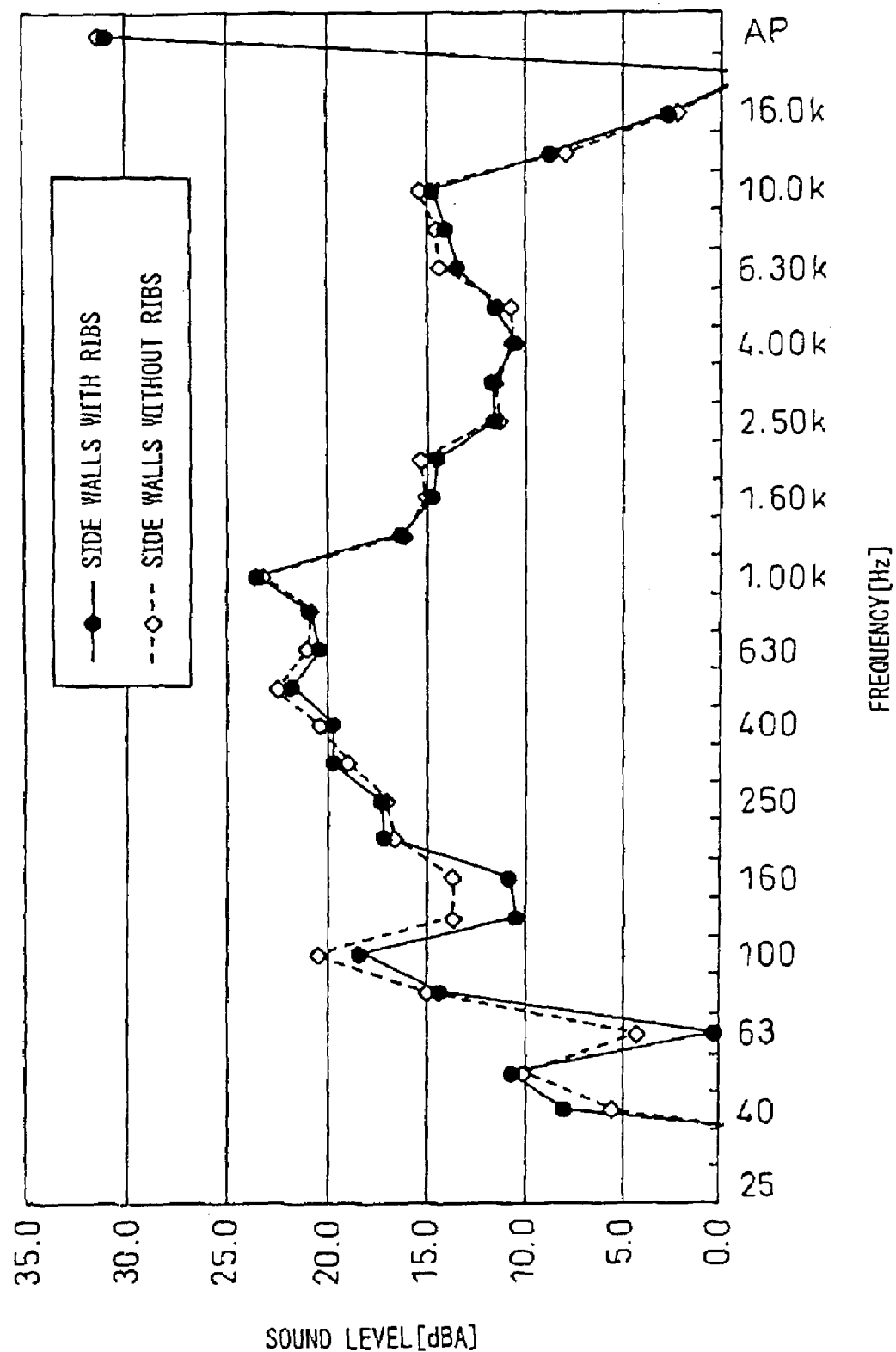
FIG. 3 is a graph in which a comparison is made between the noise level of the oxygen concentrating apparatus of the present invention and the noise level of the oxygen concentrating apparatus of the prior art, wherein the comparison is made in each frequency region.

A portion of the remaining air in the lower space in the housing 12 is sucked by the cooling fan 36 and flows into the upper space via the cooling air passage 22a of the partition wall 22. When this air passes in the neighborhood of the compressor 30, the compressor 30 is cooled by the air. After the air has cooled the compressor 30, it passes through the cooling fan 36. Then, the air is discharged from the exhaust port 12b to the outside via the connecting pipe 28 and the exhaust duct 60.

the comparison is made in each frequency region. Referring to FIG. 3, it can be understood that the sound pressure level is decreased in the low frequency region of 100 to 400 Hz according to the present invention.

On Table 1 shown below, a comparison is made between the present invention and Comparative Examples 1 to 3 with respect to the effect of reducing the noise in the exhaust duct and the pressure loss. In the experiment, an oxygen concentrator was used in which PSA system having 12 adsorbing cylinders filled with zeolite was provided. This oxygen concentrator was capable of generating oxygen enriched gas, the concentration of which was not less than 90%, by the volume of $3 \times 10^{-3}$ m$^3$/min at the maximum. The exhaust duct 60 of the present invention used for the experiment included: a rectangular cross section; one bend section; a cross section of 18 cm$^3$; an outer shell 62 made of ABS, the total length of which was 400 mm; and a sound absorbing member 64 made of soft urethane foam which was stuck on the inner face of the outer shell 62. Concerning the thickness t of the sound absorbing member 64, the thickness t was 15 mm on the side wall 1, the thickness t was 10 mm on the side wall 2, the thickness t was 5 mm on the side wall 3, and the thickness t was 10 mm on the side wall 4.

TABLE 1

|  | Present Invention | Comparative Example 1 | Comparative Example 2 | Comparative Example 3 |
|---|---|---|---|---|
| Flow Rate of Oxygen Enriched Gas ($\times 10^{-3}$ m$^3$/min) | 3 | 3 | 3 | 3 |
| Oxygen Concentration (%) | 93 | 93 | 93 | 93 |
| Number of Bend Section of Exhaust Duct | 1 | 3 | 1 | 1 |
| Cross Sectional Area of Exhaust Duct (cm$^2$) | 18 | 25 | 9 | 18 |
| Length of Exhaust Duct (mm) | 400 | 700 | 400 | 600 |
| Thickness of Sound Absorbing Material (mm) | side wall 1: 10<br>side wall 2: 15<br>side wall 3: 5<br>side wall 4: 10 | side wall 1: 10<br>side wall 2: 10<br>side wall 3: 10<br>side wall 4: 10 | side wall 1: 10<br>side wall 2: 15<br>side wall 3: 5<br>side wall 4: 10 | side wall 1: 10<br>side wall 2: 15<br>side wall 3: 5<br>side wall 4: 10 |
| Noise Level (dB (A)) | 30.5 | 29.0 | 31.0 | 31.0 |
| Pressure Lose (Pa) | 45.1 | 98.1 | 78.5 | 68.6 |
| Volume of Housing ($\times 10^{-3}$ m$^3$) | 53 | 65 | 58 | 58 |

As described before, according to the prior art in which the rib 20a is not formed on the sound insulation box 20, the side wall of the sound insulation box is vibrated in the low frequency region of 100 to 400 Hz by the pressure fluctuation caused in the sound insulation box by the noise which is generated when the compressor 30 is started and the air is supplied to the oxygen concentrator 40. On the other hand, according to the present invention, since the rib 20a is formed on the side wall of the sound insulation box 20, the rigidity of the side wall is enhanced. Therefore, it becomes possible to reduce the vibration of the side wall of the sound insulation box 20. FIG. 3 is a graph in which a comparison is made between the noise level of the oxygen concentrating apparatus 40 of the present invention and the noise level of the oxygen concentrating apparatus of the prior art, wherein As can be understood from Table 1, in the case of Comparative Example 1 having three bent portions, the noise level is 29.0 dB(A). Therefore, it is possible to reduce the noise level as compared with the present invention. However, since the number of the bent portions is increased, the total length of the duct is extended. Accordingly, it is necessary to extend the inner volume of the housing. In the case of Comparative Example 2 in which the cross sectional area of the duct is reduced, since the pressure loss of the exhaust duct is increased, it is necessary to extend a capacity of the cooling fan. Accordingly, the inner volume of the housing must be increased. Further, when the length of the duct is increased like the case of Comparative Example 3, the inner volume of the housing must be increased, and it becomes difficult to reduce the noise level.

The invention claimed is:

1. An oxygen concentrating apparatus for generating oxygen enriched gas by adsorbing and separating nitrogen gas from air, comprising:
   an oxygen concentrator having an adsorption cylinder filled with adsorbent for adsorbing nitrogen gas, also having an air inlet port, an oxygen outlet port and a nitrogen gas outlet port;
   a compressor for supplying compressed air from the air inlet port;
   a sound insulation box, which surrounds the compressor, for reducing noise generated from the compressor, ribs being formed on a side wall of the sound insulation box;
   a cooling fan for introducing air into the sound insulation box so as to cool the compressor by the introduced air;
   a housing surrounding the oxygen concentrator and the sound insulation box; and
   an exhaust duct arranged in the housing, for guiding the exhaust discharged from the cooling fan to the outside of the housing.

2. An oxygen concentrating apparatus according to claim 1, wherein the rib is diagonally provided on a side wall of the sound insulation box.

3. An oxygen concentrating apparatus according to claim 2, wherein a horizontal partition wall is provided in the sound insulation box, an inner space of the sound insulation box is divided into an upper and a lower space by the partition wall, the compressor is set on an upper face of the partition wall in the upper space, and the cooling fan is attached to an upper portion of the compressor in the upper space.

4. An oxygen concentrating apparatus according to claim 3, wherein an air inlet opening is formed on the side wall at a position lower than the partition wall.

5. An oxygen concentrating apparatus according to claim 4, wherein the compressor includes a suction pipe which penetrates the Partition wall so that the suction pipe can be communicated with the lower space.

6. An oxygen concentrating apparatus according to claim 5, wherein the partition wall includes a cooling air passage for communicating the upper space with the lower space, a portion of the air in the lower space flows into the upper space via the cooling air passage so as to cool the compressor, and the air is discharged outside the housing via the exhaust duct by the cooling fan.

7. An oxygen concentrating apparatus according to claim 3, wherein a nitrogen gas outlet port of the oxygen concentrator is communicated with an upper space of the sound insulation box.

8. An oxygen concentrating apparatus according to claim 1, wherein an air inlet is formed on the side wall of the housing, an exhaust port is formed on the bottom wall of the housing, and the exhaust duct is communicated with the exhaust port.

9. An oxygen concentrating apparatus according to claim 8, wherein an electric control unit for controlling the compressor, the cooling fan and the oxygen concentrator is attached to an inner face of a top wall of the housing, and a deflecting plate, which makes the air flowing from the air inlet into the housing flow toward the electric control unit, is arranged in the housing.

10. An oxygen concentrating apparatus according to claim 8, wherein the exhaust duct includes a hollow outer shell composed of a substantially L-shaped hollow member having a horizontal portion and a perpendicular portion connected to one end portion of the horizontal portion via one bend section and also includes a sound absorbing member of 2 to 20 mm thickness which is stuck onto an inner face of the outer shell,
   the other end of the horizontal portion of the outer shell is communicated with an air outlet of the cooling fan, a lower end of the perpendicular portion of the outer shell is arranged in the housing so that it can be communicated with the exhaust port, and the cross-sectional area of the outer shell is 12 to 20 $cm^2$ and the length of the outer shell is 350 to 450 mm.

11. An oxygen concentrating apparatus for generating oxygen enriched gas by adsorbing and separating nitrogen gas from air, comprising:
   an oxygen concentrator having an adsorption cylinder filled with adsorbent for adsorbing nitrogen gas, also having an air inlet port, an oxygen outlet port and a nitrogen gas outlet port;
   a compressor for supplying compressed air from the air inlet port;
   a sound insulation box, which surrounds the compressor, for reducing noise generated from the compressor, ribs being formed on a side wall of the sound insulation box;
   a cooling fan for introducing air into the sound insulation box so as to cool the compressor by the introduced air;
   a housing surrounding the oxygen concentrator and the sound insulation box; and
   an exhaust duct arranged in the housing, for guiding the exhaust discharged from the cooling fan to the outside of the housing, wherein
   the exhaust duct includes a hollow outer shell having a horizontal portion and a perpendicular portion, which is connected to one end portion of the horizontal portion via one bend section so that the hollow outer shell can be extended into a substantial L-shape, and also includes a sound absorbing member of 2 to 20 mm thickness which is stuck onto an inner face of the hollow outer shell, the other end portion of the horizontal portion of the hollow outer shell is communicated with an outlet of air of the cooling fan, a lower end portion of the perpendicular portion is arranged in the housing so that it can be communicated with the exhaust port, and a cross sectional area of the exhaust duct is 12 to 20 $cm^2$ and the length of the exhaust duct is 350 to 450 mm.

12. An oxygen concentrating apparatus according to claim 11, wherein a horizontal partition wall is arranged in the sound insulation box, an inner space of the sound insulation box is divided into an upper space and lower space, the compressor is set on an upper face of the partition wall in the upper space, and the cooling fan is attached in an upper portion of the compressor.

13. An oxygen concentrating apparatus according to claim 12, wherein an air inlet opening is formed at a position lower than the partition wall on the side wall of the sound insulation box.

14. An oxygen concentrating apparatus according to claim 13, wherein the compressor includes a suction pipe penetrating the partition wall so that the suction pipe can be communicated with the lower space.

15. An oxygen concentrating apparatus according to claim 14, wherein the partition wall includes a cooling air passage for communicating the upper space with the inner space, and a portion of the air in the lower space flows into the upper space via the cooling air passage and cools the compressor and is discharged by the cooling fan to the outside of the housing via the exhaust duct.

16. An oxygen concentrating apparatus according to claim 13, wherein a nitrogen gas outlet port of the oxygen concentrator is communicated with the upper space of the sound insulation box.

17. An oxygen concentrating apparatus according to claim 11, wherein an air inlet is formed on the side wall of the housing, an exhaust port is formed on the bottom wall of the housing, and the exhaust duct is communicated with the exhaust port.

18. An oxygen concentrating apparatus according to claim 11, wherein an electric control unit for controlling the compressor, the cooling fan and the oxygen concentrator is attached onto the inner face of the top wall of the housing, and
  a deflecting plate for making the air, which has flowed from the air inlet into the housing, flow toward the electric control unit is arranged in the housing.

* * * * *